Figure 1:
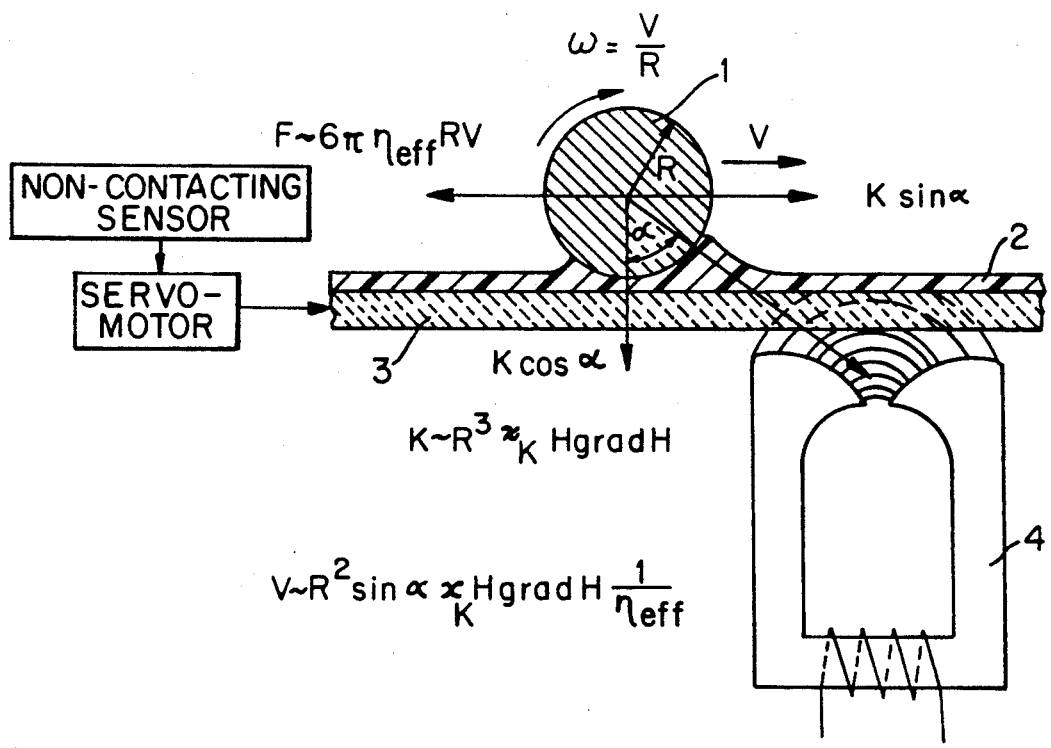

United States Patent

Laun et al.

Patent Number: 5,212,981
Date of Patent: May 25, 1993

[54] METHOD OF AND APPARATUS FOR MEASURING THE VISCOSITY OF MATERIALS

[75] Inventors: Martin Laun, Ludwigshafen; Wolfgang Göring, Münster; Theodora Dirking, Münster; Hans-Joachim Streitberger, Münster, all of Fed. Rep. of Germany

[73] Assignee: BASF Lacke & Farben AG, Münster, Fed. Rep. of Germany

[21] Appl. No.: 536,595

[22] PCT Filed: Nov. 24, 1988

[86] PCT No.: PCT/EP88/01070
§ 371 Date: Aug. 31, 1990
§ 102(e) Date: Aug. 31, 1990

[87] PCT Pub. No.: WO89/06352
PCT Pub. Date: Jul. 13, 1989

[30] Foreign Application Priority Data

Jan. 11, 1988 [DE] Fed. Rep. of Germany ....... 3800474

[51] Int. Cl.$^5$ .............................................. G01N 11/02
[52] U.S. Cl. .................................. 73/54.01; 73/54.23
[58] Field of Search ............... 73/54, 59, 54.01, 54.23, 73/54.15

[56] References Cited

U.S. PATENT DOCUMENTS 4,627,272 12/1986 Wright ..................... 73/54
4,781,808 11/1988 Geist et al. ............... 204/181.7
5,040,410 8/1991 Chu et al. ................. 73/54

FOREIGN PATENT DOCUMENTS 0144437 6/1985 European Pat. Off. .
3420341 12/1985 Fed. Rep. of Germany .

OTHER PUBLICATIONS

Revue de Physique Appliquee, Band 19, Nr. 3, Marz 1984, (Orsay, FR).
M. Adams et al.: "Magnetorheometre a bille": Seiten 253–264.
Farbe and Lack, 83. Jahrgang, Nr. 4, 1977, (Hannover, DE) W. Goring et al.: "Zur Messung der Viskositat von Lackfilmen wahrend des Abulft-und Einbrennvorganges", pp. 270–277.

Primary Examiner—Herbert Goldstein
Assistant Examiner—Raymond Y. Mah
Attorney, Agent, or Firm—Kenyon & Kenyon

[57] ABSTRACT

The invention relates to a process and device for measuring the effective viscosity and the elastic properties of coatings. Known measuring processes and measuring devices based on the "rolling ball method" suffer from drawbacks, namely run formation and sinking of the relatively heavy solvent vapors, due to the inclination of the coated sheet metal. To overcome these drawbacks, rolling movements are imparted to a magnetizable ball (1) displaced from its rest position in a magnetic field, during movement of the horizontally disposed substrate, under the influence of the field gradient of a permanent magnet or electromagnet (4) located below the substrate. The rolling movements are used as the basis for the measurements.

26 Claims, 1 Drawing Sheet

METHOD OF AND APPARATUS FOR MEASURING THE VISCOSITY OF MATERIALS

The invention relates to a method of measuring the effective viscosity and the elastic properties of coatings and to an apparatus for carrying out this method.

Very high demands are placed on the corrosion protection and the optical properties of industrial paints. The paints must flow well, and may not have any surface imperfections, such as solvent poppings and craters, nor any formation of runs. The edge coverage by the coating must be as good as possible. Essentially, these required properties depend on the temporal variation of the flow behavior of the applied coating during drying. The flow behavior and its temporal variation are determined by the qualitative and quantitative composition of the recipe of the coating material, and by the conditions during the drying process (duration of the flash-off phase, stoving time, stoving temperature, etc).

The measurement of the flow behavior of coatings using the "rolling sphere method" stems from work done in 1936. Since then, this measurement method has frequently been employed. A computer-controlled measuring apparatus, which is described in DE 3,420,341 C2, allows the apparent viscosity to be measured quantitatively during the flash-off and stoving process. In this connection, a coated plate is inclined at a defined angle (e.g. 30°) to the horizontal, and the rolling motion of a steel sphere in the paint film is compensated by rotating the plate with the aid of a motor drive about an axis which is perpendicular to its plane and passes through its center. In conjunction with an electrical unit, a punctiform light source and an associated light detector serve to control the motor drive, the motor rotating the coated plate against the direction of motion of the sphere, in order to keep the latter at approximately the same location in the vertical direction. The speed of rotation of the coated plate is inversely proportional to the viscosity of the coating. In this way, the film viscosity can be measured as a function of the time or temperature of the film.

This measurement method has the disadvantage that the inclination of the coated plate causes both the formation of runs, and also the settling of the relatively heavy solvent vapors during the process of physical drying. Thus, it can happen that the steel spheres employed for measurement come into regions of different layer thickness, which manifests itself unfavorably in the measurement accuracy.

Known from the teachings of EP-A1-0 144 437 is a device for measuring the viscoelasticity of low viscose imide, whereby a ball within the liquid is moved by magnetic forces in an oscillating manner with high frequency. The liquid and the ball are located in a sealed container. The liquid must be transparent. The device is not suitable for measuring the effective viscosity and the elastic properties of coatings during the exhaust and annealing phase.

It is the object of the invention to create a measurement method and a measurement apparatus, with which the disturbing formation of runs, and also the settling of solvent vapors are avoided, and with which the magnitude of the force acting on the sphere can be adjusted over a wide range, so that an expansion of the viscosity measuring range can be achieved.

This object, on which the invention is based, is achieved by means of the proposal according to the invention that the coated substrate can be arranged horizontally, and that thus both the disturbing formation of runs and also the settling of solvent vapors are avoided. The magnitude of the magnetic force acting on the sphere composed of ferromagnetic material can be adjusted over a wide range, which signifies a substantial expansion of the viscosity measuring range from approximately 10 mPas to approximately 1000 Pas or more. As compared with the previous measuring apparatuses, it is therefore technically possible, during the stoving process of the coating, to encompass a larger, previously unknown range of viscosity.

The measurement of the speed of the sphere in the viscous paint film can take place on-line, and the measurement method can therefore be fully automated.

Figure 2:
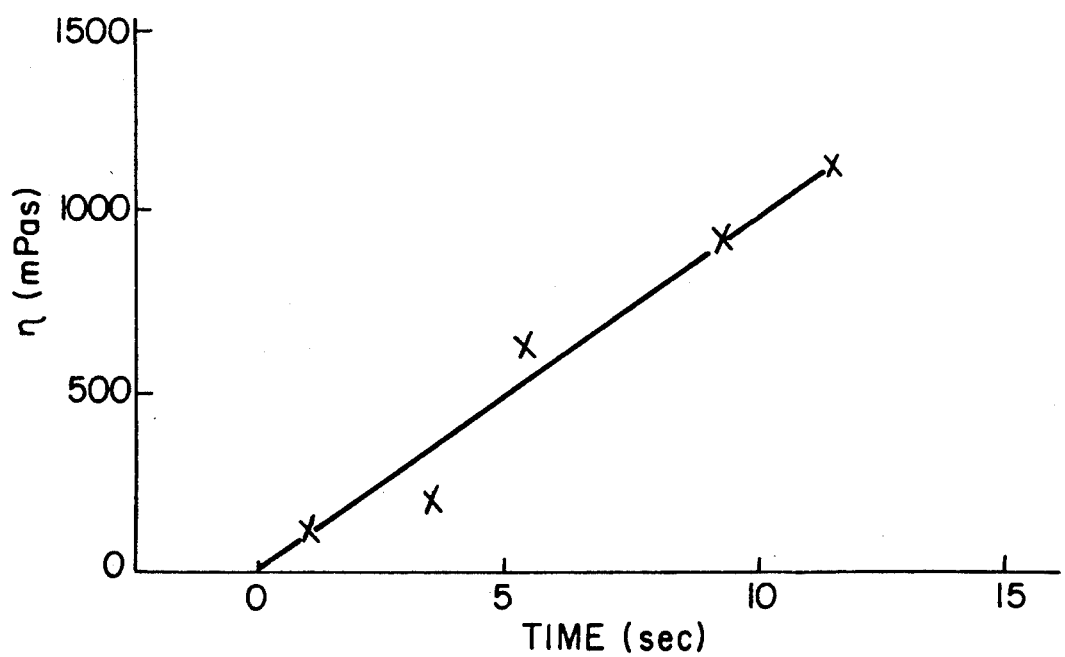

An illustrative embodiment of the invention is explained below with reference to the drawings, in which FIG. 1 shows a sketch of the magnetic measurement arrangement, and FIG. 2 shows a curve obtained with the measurement apparatus according to the invention.

The essential parts of the measurement apparatus are represented in FIG. 1. A magnetizable sphere 1 is excited to a rolling motion in a coating 2 in conjunction with the movement of a horizontally arranged substrate 3 consisting of non-ferromagnetic material, e.g. glass, under the influence of the field gradient of a permanent magnet or electromagnet 4 arranged underneath the substrate 3. Given fixed magnets 4, the speed v of the substrate 3 is regulated in such a way that the sphere 1 is held rolling at a constant separation $\Delta x$ from the position of rest. In this connection, the position of the sphere is detected by a non-contacting sensor. This corresponds to a test with constant magnetic driving force on the sphere 1, there being established a rolling speed which is proportional to the reciprocal of the effective coating viscosity. The motion of the substrate 3 caused by a servomotor drive can either be a purely linear motion or a rotation (circular path). However, it can also be a combination of the two (e.g. spiral path).

The generation of the field by an electromagnet 4 has the advantage that the force, acting on the sphere 1 can be varied and regulated over a wide range via the coil current. This signifies a substantial advantage over the previous measuring apparatuses, in which a constant force, namely gravity, acts on the rolling sphere. According to the invention, there is therefore an extension of the viscosity measuring range to values between 10 mPas and 1000 Pas or more.

However, the measurement method according to the invention includes still further possiblities for adjusting the driving force or rolling speed of the sphere 1 to the variable coating viscosity:

a) selection of a different displacement $\Delta x$
b) selection of a different substrate thickness
c) selection of a different pole shoe geometry
d) selection of a different sphere diameter
e) selection of a sphere material having a different magnetic permeability.

Thus, the following advantages arise by comparison with the mode of procedure which belongs to the prior art and operates with an inclined plate:

1. No formation of runs in the coating, e.g. a paint film.
2. No settling of the relatively heavy solvent vapors, or or no formation of solvent traps.
3. On-line measurement of the effective viscosity.

4. The magnitude of the magnetic force acting on the sphere 1 can be adjusted over a wide range.
5. Viscosity range 10 mPas to 1000 Pas or more.
6. Lateral focussing of the sphere 1 by the magnetic field.
7. The measurement method can be fully automated.
8. The measurement method can be extended to oscillatory rolling motions in order to measure the viscoelasticity.

FIG. 2 shows a graph obtained with the magnetic measuring apparatus described. FIG. 2 shows a curve diagram obtained with the described measuring device. For oil films (film thickness 250 μm) of different viscosity the sphere rolling time is represented under the influence of the magnetic field, whereby a permanent magnet was used. Spheres 1 of soft iron were used, which had a diameter of 2.5 mm. Five calibration oils of different viscosity in the range from 80 to 1200 mPas were selected for the measurements. The oil films were produced with a drawing straight-edge on glass plates 3 of thickness 1 mm. The measuring temperature amounted to 20.0° C., and the length of the measuring distance Δ x to 3 cm.

The physico-mathematical relationship which is given in FIG. 1 signifies that the rolling speed of the sphere 1 is inversely proportional to the effective viscosity of the coating 2. This theoretically derivable linear relationship between the measuring time t (or rolling speed v of the sphere), together with the viscosity of the coating 2, e.g. the oil films, is experimentally confirmed by the measurement results according to FIG. 2. The upshot is that the magnetic measurement method can be used for the required application, namely the determination of the viscosity of coatings.

In the stoving phase of the coating in the temperature range from 200° C. (or also up to 300° C.) account must be taken of the decrease of the magnetization of the ferromagnetic iron spheres. This dependency of the magnetic susceptibility on temperature is known, and is taken into account via the software by means of the computer during calculation of the effective viscosity.

The measuring apparatus can be extended in such as way that the sphere 1 executes oscillatory rolling motions under the additional influence of a lateral alternating magnetic field of an electromagnet 4, the elastic properties of coatings 2 can be determined in this way. The real and imaginary parts of the complex modulus of rigidity (storage modulus and loss modulus, respectively) can be determined as a function of the frequency.

We claim:

1. An apparatus for measuring the effective viscosity and the elastic properties of coatings during a flash-off phase and a stoving phase comprising:
   a horizontal coated substrate, the substrate including a plate of non-ferromagnetic material;
   a sphere on the coated substrate composed of a ferromagnetic material and having a sphere diameter of 1 to 10 mm;
   a servomotor drive for moving the coated substrate; and
   a magnet underneath the coated substrate, said magnet causing magnetic forces to act on the sphere.

2. The apparatus according to claim 1 wherein the magnet is a permanent magnet.

3. The apparatus according to claim 1 wherein the magnet is an electromagnet.

4. The apparatus according to claim 1, wherein the sphere is composed of steel, and has a sphere diameter of 2.5 mm.

5. The apparatus according to claim 1 wherein the substrate executes a substantially linear motion.

6. The apparatus according to claim 1 wherein the substrate executes a substantially rotational motion.

7. The apparatus according to claim 1 wherein the substrate executes a combination of a linear motion and a rotational motion.

8. The apparatus according to claim 1 wherein the electromagnet is regulable in order that the force acting on the sphere can be varied and regulated over a wide range via a coil current.

9. The apparatus according to claim 1 wherein the ferromagnetic sphere material includes compositions of different magnetic susceptibility.

10. The apparatus according to claims 1 wherein the non-ferromagnetic material for the substrate includes glass.

11. The apparatus according to claim 1 wherein the diameter of the sphere is 1.5 to 4 mm.

12. A method of measuring the effective viscosity of coatings during the flash-off phase and stoving phase comprising:
   placing a magnetizable sphere on a horizontal coated substrate, the substrate being at a fixed distance above a magnet and the center of the sphere being at its position of rest due to the magnetic forces acting on the sphere;
   moving the substrate at a speed such as to cause said center of the sphere to be displaced from said position of rest, wherein the magnetic forces acting on the sphere cause the sphere to undergo a rolling motion toward said position of rest;
   regulating the speed of the substrate such that said center of the sphere is held at a constant separation from said position of rest, the position of the sphere being detected by a non-contacting sensor that controls said speed of the substrate; and
   using said speed of the substrate to calculate the effective viscosity of the coating on said substrate.

13. The method according to claim 12 wherein the magnet is a permanent magnet.

14. The method according to claim 12 wherein the magnet is an electromagnet.

15. A method of measuring the effective viscosity of coatings during the flash-off phase and stoving phase comprising:
   placing a horizontal coated substrate at a fixed distance above a magnet;
   placing a magnetizable sphere on the coated substrate at a position away from the position of rest the center of the sphere would have on a non-moving substrate due to the magnetic forces acting on the sphere;
   moving the substrate at a speed such as to cause the sphere to undergo a rolling motion toward said position of rest;
   regulating the speed of the substrate such that said center of the sphere is held at a constant separation from said position of rest, the position of the sphere being detected by a non-contacting sensor that controls said speed of the substrate; and
   using said speed of the substrate to calculate the effective viscosity of the coating on said substrate.

16. The method according to claim 15 wherein the magnet is a permanent magnet.

17. The method according to claim 15 wherein the magnet is an electromagnet.

18. The method according to claim 12 wherein the sphere is composed of steel, and has a sphere diameter of from about 1.5 to about 4 mm.

19. The method according to claim 18 wherein the sphere diameter is about 2.5 mm.

20. The method according to claim 12 wherein the substrate executes a substantially linear motion.

21. The method according to claim 12 wherein the substrate executes a substantially rotational motion.

22. The method according to claim 12 wherein the substrate executes a combination of a linear and a rotational motion.

23. The method according to claim 14 wherein the electromagnet is regulable in order that the magnetic force acting on the sphere can be varied and regulated over a wide range via a coil current.

24. The method according to claim 12 wherein the magnetizable sphere comprises compositions of different magnetic susceptibility.

25. The method according to claim 12 wherein the substrate comprises a non-ferromagnetic material.

26. The method of claim 25 wherein the non-ferromagnetic material includes glass.

* * * * *